United States Patent [19]

Noda et al.

[11] Patent Number: 5,439,674

[45] Date of Patent: Aug. 8, 1995

[54] HAIR COSMETIC MATERIAL

[75] Inventors: Isao Noda; Suguru Tsubaki, both of Kanagawa, Japan

[73] Assignee: OSi Specialties, Inc., Danbury, Conn.

[21] Appl. No.: 181,604

[22] Filed: Jan. 14, 1994

Related U.S. Application Data

[63] Continuation of Ser. No. 929,376, Aug. 14, 1992, abandoned.

[51] Int. Cl.$^6$ .............................................. A61K 7/075
[52] U.S. Cl. ........................ 424/70.12; 424/70.122; 424/7.22; 424/70.24
[58] Field of Search ............. 424/78.08, 70.12, 70.122, 424/70.24

[56] References Cited

U.S. PATENT DOCUMENTS

| | | |
|---|---|---|
| 4,342,742 | 8/1982 | Sebag . |
| 4,378,345 | 3/1983 | Okumura . |
| 4,601,299 | 7/1986 | Wolfram . |
| 4,844,888 | 7/1989 | Zawadzki . |
| 4,915,938 | 4/1990 | Zawadzki ............................. 424/70 |

FOREIGN PATENT DOCUMENTS

| | | |
|---|---|---|
| 174097 | 8/1985 | European Pat. Off. . |
| 0174697 | 12/1986 | European Pat. Off. . |
| 6212712 | 1/1987 | Japan . |
| 1172313 | 12/1987 | Japan . |
| 1190619 | 1/1988 | Japan . |
| 1296021 | 1/1969 | United Kingdom . |

OTHER PUBLICATIONS

Derwent Abstract 007972576 Feb. 5, 1991.

*Primary Examiner*—Thurman K. Page
*Assistant Examiner*—Peter F. Kulkosky
*Attorney, Agent, or Firm*—Andrew S. Reiskind

[57] ABSTRACT

A hair set retaining cosmetic material comprising a polymer complex prepared by (1) reacting an amino group containing polysiloxane having the formula:

$$A_mR_{3-m}SiO(R_2SiO)_x(QRSiO)_ySiR_{3-n}A_n$$

wherein A is selected from the group consisting of a hydroxyl group, an alkoxy group, and an amino group containing alkylether group; R is selected from the group consisting of an alkyl group having 1 to 18 carbon atoms and a hydroxyl group; Q represents an amino containing alkyl group; m and n each represent a number of 0 to 3; x represents a number of 30 to 400; and y represents a number of 1 to 30 with an anionic group containing polymer; and (2) neutralizing a reaction product of step (1) with an alkaline compound to a neutralization ratio of 60–150%.

12 Claims, No Drawings

HAIR COSMETIC MATERIAL

This is a continuation of application Ser. No. 07/929,376 filed on Aug. 14, 1992, now abandoned.

FIELD OF THE INVENTION

This invention relates to a hair cosmetic material which gives hair glossiness, smoothness to the touch, ease of combing, flexibility or non-stiffness and, in addition, has good hair set retention and storage stability.

PRIOR ART

A hair cosmetic material such as hair setting lotion, hair spray and hair styling spray or mist typically contains a film forming polymer as a main component. For example, the following polymers have been proposed for such purposes:

1-ethenyl-2-pyrrolidinone,homopolymer
1-ethenyl-2-pyrrolidinone, copolymer with acetic acid, ethyl ester
ethene, methoxy-, copolymer with but-2-ene-1,4-dioic acid mono ethyl or mono butyl ester
acetic acid, ethenyl ester, homopolymer carboxylated
2-butenoic acid, copolymer with acetic acid, ethenyl ester
alkyl 2-propenoate, copolymer with alkyl 2-methyl-2-propenoate
1-(hydroxymethyl)-5,5-dimethyl hydantoin, homopolymer
dialkylamino alkyl 2-methyl-2-propenoate, homopolymer quaternized
1-ethenyl-2-pyrrolidinone, copolymer with dialkyamino alkyl 2-methyl-2-propenoate
2-hydroxyethyl cellulose, quaternary ammonium modified
cationic polysaccharide
1-ethenyl-2-pyrrolidinone, homopolymer quaternized
siliconized cationic polymer
quaternized polyurethane
1-ethenyl-2-pyrrolidinone, copolymer with 2-(dimethylamino)ethyl 2-methyl-2-propenoate, compound with dialkyl sulfate
quaternary ammonium salt and quaternary sulfonic acid salt containing polymer or copolymer
3-(dimethylamino)propyl 2-methyl-2-propenoate, homopolymer or copolymer compound with dialkyl sulfate
carboxylic acid (salt) containing monomer, copolymer with tertiary nitrogen containing monomer
2-propenoic acid, copolymer with vinyl pyridine
quaternized carboxylic acid (salt) containing monomer, copolymer with tertiary nitrogen containing monomer
octyl acrylicamide, acrylate, butylaminoethyl methacrylate, acrylic acid copolymer
carboxyl group and quaternary ammonium salt containing monomer, polymer or copolymer
N-methacryloyl-N,N'-dimethyl ammonium α-N methylcarboxylicbetaine methacrylic acid alkylester copolymer However, these polymers or copolymers exhibit an insufficient hair set retaining property and/or give hair poor gloss or lack smoothness or softness to the touch. In some hair formulations, they give hair a sticky or starchy feeling.

To improve the above deficiencies, it has been suggested that the above-mentioned hair set polymers be used in combination with an oil, ester oil and hydrocarbon oil. However, these combinations give hair a greasy, oily feeling and exhibit poor hair set retaining ability.

Since the oils are incompatible with water, surface active agents must be used which results in hair with poor feel.

Another way to improve the above deficiencies, is to employ the combination of an amino group containing organodimethyl polysiloxane with a cationic surface active agent and an amphoteric polymer. This polysiloxane has good properties such as giving hair gloss, good compatibility with water and imparts smoothness to hair. (Japanese laid open patent No. 01-190619).

As a hair set retaining polymer, an anionic polymer is desirable since it exhibits good hair set retaining capability and an amphoteric polymer is not suitable since it exhibits poor hair set retaining capability, hence, they are not usually used as a hair set polymer.

It is presumed that above JP-01-190619 was proposed because the combination of amino siloxane with anionic polymer forms a gel which precipitates and the combination of aminosiloxane with amphoteric polymer does not result in such gelation or precipitation.

Cationic polymers exhibit insufficient hair set property.

There is an on-going need for a hair cosmetic material having properties such as good fitness with hair, hair glossiness, smoothness of the hair to touch, ease of combing and flexible (non-stiff) finish which are associated with amino group containing organopolysiloxanes and other desirable hair set retaining properties which are associated with the anionic polymer, without the adverse effect of gelation or precipitation.

SUMMARY IF THE INVENTION

It is an object of this invention to provide a hair cosmetic having excellent hair set retaining property.

A hair cosmetic material of the invention is characterized by a polymer complex prepared by (1) reacting an amino group containing polysiloxane expressed by the following general formula.

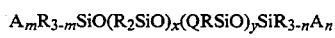

wherein
A is selected from the group consisting of a hydroxyl group, an alkoxy group, and an amino containing alkylether group;
R is selected from the group consisting of an alkyl group having 1 to 18 carbon atoms and a hydroxyl group;
Q represents an amino containing alkyl group;
m and n each represent a number of 0–3;
x represents a number of 30–400; and
y represents a number of 1–30 with an anionic group polymer, and then (2) neutralizing a reaction product of step (1) with an alkaline compound for a neutralization ratio of 60–150%.

DETAILED DESCRIPTION OF THE INVENTION

It has been conventionally known that the combination of a cationic polymer (amino group containing organopolysiloxane exhibit weak cationic property) with anionic polymer forms a gel in the solvent which gel precipitates, and hence, the two components are not used as a hair cosmetic material.

However, the inventors of this invention have discovered that it is possible to produce a soluble copolymer complex by reacting a specific molecular structure aminopolysiloxane with a specific anionic polymer which, if followed by neutralization of copolymer complex eliminates gel formation or precipitation and the copolymer so formed has excellent cosmetic hair properties.

That is, the present invention provides a hair set retaining cosmetic material comprising a polymer complex prepared by (1) reacting amino group containing polysiloxane of the general formula:

$$A_mR_{3-m}SiO(R_2SiO)_x(QRSiO)_ySiR_{3-n}A_n$$

wherein
A is selected from the group consisting of a hydroxyl group, an alkoxy group, and an amino group containing alkylether group;
R is selected from the group consisting of an alkyl group having 1 to 18 carbon atoms and a hydroxyl group;
Q represents an amino group containing alkyl group;
m and n each represent a number of 0–3;
x represents a number of 30–400; and
y represents a number of 1–30
with an anionic group polymer, and then (2) neutralizing a reaction product of step (1) with an alkaline compound for a neutralization ratio of 60–150%.

The amino group containing polysiloxane of this invention is a polymer expressed by the above chemical formula and A, R, Q, m, n, x and y are defined as in the above formula and the numerical scope is as set forth in the above formula. When an amino group containing polysiloxane outside the range set forth in the above formula is employed, the copolymer complex formed by reacting with anionic polymer forms a precipitate in the solution, which is not desirable for this invention.

The anionic polymer useful in this invention, is illustrated by the following polymers:
1-ethenyl-2-pyrrolidinone, homopolymer
1-ethenyl-2-pyrrolidinone, copolymer with acetic acid, ethenyl ester
ethene, methoxy-, copolymer with but-2-ene-1,4-dioic acid acid mono ethyl or mono butyl ester
acetic acid, ethenyl ester, homopolymer carboxylated
2-butenoic acid, copolymer with acetic acid, ethenyl ester
2-butenoic acid, copolymer with alkyl 2-methyl-2-propenoate
diacetone acrylamide, copolymer with alkyl 2-propenoate or with alkyl 2-methyl-2-propenoate or with 2-propenoic acid or with 2-methyl-2-propenoic acid
1-(hydroxymethyl)-5,5-dimethyl hydantoin, homopolymer In a preferred embodiment of the present invention the anionic polymer is a carboxylate group containing polymer.

The copolymer complex of this invention prepared by reacting 100 parts by weight of the amino group containing organopolysiloxane with 20 parts by weight to 5,000 parts by weight of the anionic polymer.

If less than 20 parts by weight of anionic polymer are employed, the hair set retaining property is insufficient and if more than 5,000 parts by weight of anionic polymer are used, the hair cosmetic material does not impart hair gloss, smooth touch, ease of combing and flexible, non-stiff finish.

The copolymer complex of the amino group containing organopolysiloxane with the anionic polymer of this invention are neutralized with an alkaline compound for a neutralization ratio of 60% to 150%.

Illustrative alkaline compounds that can be employed in this invention include 2-amino-2-methyl propanol, 2-amino-2-methyl-1,3-propanediol and triisopropanol amine.

If the neutralization ratio is less than 60%, the polymer complex does not dissolve into the solution, and if more than 150% of the neutralization ratio is used, the hair cosmetic material exhibits poor hair set retaining properties and gives hair sticky or starchy feeling.

The hair cosmetic material of this invention employs the above-described polymer complex as a main component, and can additionally employ a carrier component comprising a lower alcohol or mixture of water with a lower alcohol and so that the complex can be applied in the form of spray, aerosol, liquid or mousse.

The hair cosmetic material which is applied to the hair, according to this invention, is prepared by blending the above described complex with one or more of the following: an oil which is used as a component of the usual hair cosmetics (camellia oil, rapeseed oil, sesame oil, safflower oil, cottonseed oil, castor oil, soybean oil, coconut oil, palm oil, beeswax, montanic wax, lanolin, squalane, silicone oil, etc.), a surface active agent (alkyl benzenesulfonate, polyoxyalkylene alkylsulfate ester, alkylsulfate ester, alkanesulfonate, alkyl ethoxycarboxylate, succinic derivatives, alkylemine oxide, imidazoline compounds, polyoxyethylene alkyl or alkenyl ether, polyoxyethylene alkyl phenyl ether, higher fatty acid alkanolamide or its alkylene oxide addition products, etc.), high-molecular compounds (hydroxyethyl cellulose, hydroxypropyl cellulose, hydroxypropyl methyl cellulose, methyl cellulose), antioxidants, UV absorbers, moisture retaining agents, perfumes, dyes, pigments, coloring matters, preservatives, vitamins, hormones, deodorants, binders, etc.

The hair cosmetic material of this invention is used for a variety of hair, including artificial hair, human hair as well as an animal fur and feathers of pets such as, for example, dogs, cats, monkeys, macaws, and canaries.

EXAMPLES

Following are examples of this invention. (Examples of synthesizing the polymer complex)

Synthesis—Example 1

Twenty-four (24) parts by weight of an anionic polymer (PLASCIZE L-53, available from UJI Chemical), a diacetone acrylamide copolymer with alkyl 2-propenoate 50% solution in ethyl alcohol was added to eighty (80) parts by weight of ethyl alcohol and agitated at room temperature.

Three (3) parts by weight of an amino group containing polysiloxane expressed by following chemical formula was added to the above mixture and agitated at room temperature.

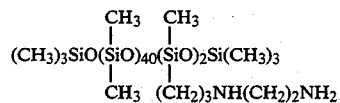

The resulting mixture was refluxed for three (3) hours at eighty (80) degrees Centigrade under a nitrogen gas atmosphere with agitation to distill the solvent (ethanol) and to obtain fifteen (15) parts by weight solid in mixture.

The reaction product so obtained was neutralized with 2-amino-2-methylpropanol for a neutralization ratio of 70% under agitation to obtain polymer complex (1).

Synthesis—Example 2

Twenty-four (24) parts by weight of an anionic polymer, (PLASCIZE L-53 available from UJI Chemical), a diacetone acrylamide copolymer with alkyl 2-propenoate 50% solution in ethyl alcohol was added to eighty (80) parts by weight of ethyl alcohol and agitated at room temperature.

Three (3) parts by weight of an amino group containing polysiloxane expressed by following chemical formula was added to above mixture and agitated at room temperature.

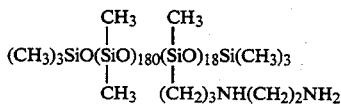

The resulting mixture was refluxed for three (3) hours at eighty (80) degrees Centigrade under a nitrogen gas atmosphere with agitating to distill the solvent (ethanol) and to obtain fifteen (15) parts by weight solid in mixture.

The reaction product so obtained was neutralized with 2-amino-2-methylpropanol for a neutralization ratio of 70% under agitation to obtain polymer complex (2).

Synthesis—Example 3

Twenty-four (24) parts by weight of an anionic polymer (PLASCIZE L-53, available from UJI Chemical), diacetone acrylamide copolymer with alkyl 2-propenoate 50% solution in ethyl alcohol was added to eighty (80) parts by weight of ethyl alcohol and agitated at room temperature.

Three (3) parts by weight of an amino group containing polysiloxane expressed by following chemical formula was added to above mixture and agitated at room temperature.

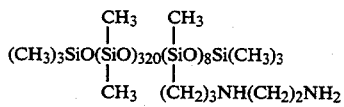

The resulting mixture was refluxed for three (3) hours at eighty (80) degrees Centigrade and under a nitrogen gas atmosphere with agitating to distill the solvent (ethanol) to obtain fifteen (15) parts by weight solid in mixture.

The reaction product so obtained was neutralized with 2-amino-2-methylpropanol, 3-propandiol for a neutralization ratio of 70% under agitation to obtain polymer complex (3).

Synthesis—Example 4

Twenty-four (24) parts by weight of anionic polymer (PLASCIZE L-53) available from UJI Chemical), an diacetone acrylamide copolymer with alkyl 2-propenoate 50% solution in ethyl alcohol was added to seventy-three (73) parts by weight of ethyl alcohol and agitated at room temperature.

Three (3) parts by weight of an amino group containing polysiloxane expressed by following chemical formula was added to above mixture and agitated at room temperature.

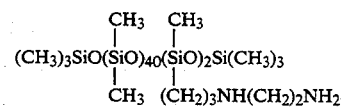

The resulting mixture was refluxed for three (3) hours at eighty (80) degrees Centigrade under a nitrogen gas atmosphere with agitating to distill the solvent (ethanol) and to obtain fifteen (15) parts by weight solid in mixture.

The reaction product so obtained was neutralized with 2-amino-2-methylpropanol for a neutralization ratio of 70% under agitation to obtain polymer complex (4).

Example 1

A hair cosmetic having the following composition was prepared:

| | |
|---|---|
| Polymer complex (1) | 10 parts by weight |
| Ethanol | 30 parts by weight |
| Water | Balance of 100 parts by weight |
| Perfume | 0.1 parts by weight |
| Preservative | 0.01 parts by weight |

Comparative Example 1

A hair cosmetic was prepared by replacing polymer complex (1) of Example 1 with the amino group containing polysiloxane used in Synthesis Example 1.

This Comparative Example 1 was performed to obtain the standard evaluation of hair cosmetic of this invention, because amino group containing polysiloxanes are known to give hair excellent gloss, smooth touch, ease of combing and a flexible, non-stiff finish.

| | |
|---|---|
| Amino polysiloxane (used in Synthesis Example 1) | 10 parts by weight |
| Ethanol | 30 parts by weight |
| Water | Balance of 100 parts by weight |
| Perfume | 0.1 parts by weight |
| Preservative | 0.01 parts by weight |

Comparative Example 2

A hair cosmetic was prepared by replacing polymer complex (1) of Example 1 with the anionic polymer used in Synthesis Example 1.

This Comparative Example 2 was done to obtain the standard evaluation of hair cosmetic of this invention, because an anionic polymers are known to give hair good hair set retaining ability.

| | |
|---|---|
| Anionic polymer (used in Synthesis Example 1) | 10 parts by weight |
| Ethanol | 30 parts by weight |
| Water | Balance of 100 parts by weight |
| Perfume | 0.1 parts by weight |

| | |
|---|---|
| -continued | |
| Preservative | 0.01 parts by weight |

Evaluation of Example 1

GLOSS: Excellent gloss was observed comparable to that of Comparative Example 1.

HAIR SET RETAINING: Excellent hair set retaining was observed comparable to that of Comparative Example 2.

SMOOTHNESS: Excellent smoothness was observed comparable to that of Comparative Example 1.

WETNESS: Excellent wetness was observed comparable to that of Comparative Example 1.

Example 2

A hair cosmetic having a composition prepared by replacing polymer complex (1) of Example 1 with polymer complex (2) synthesized by Synthesis Example 2. The composition was as follows:

| | |
|---|---|
| Polymer complex (2) | 10 parts by weight |
| Ethanol | 30 parts by weight |
| Water | Balance of 100 parts by weight |
| Perfume | 0.1 parts by weight |
| Preservative | 0.01 parts by weight |
| EVALUATION: Good results were observed comparable to that of Example 1. | |

Example 3

A hair cosmetic having a composition prepared by replacing polymer complex (1) of Example 1 with polymer complex (3) synthesized by Synthesis Example 3. The composition was as follows:

| | |
|---|---|
| Polymer complex (3) | 10 parts by weight |
| Ethanol | 30 parts by weight |
| Water | Balance of 100 parts by weight |
| Perfume | 0.1 parts by weight |
| Preservative | 0.01 parts by weight |
| EVALUATION: Good results were observed comparable to that of Example 1. | |

EVALUATION: Good results were observed comparable to that of Example 1.

Comparative Example 3

In accordance with the procedure set forth in Synthesis Example 1, two tests were conducted by changing the neutralization ratio from 70% to 50% and 170%, respectively, using the same product obtained by reacting amino-polysiloxane with anionic polymer defined in Synthesis Example 1.

EVALUATION:

Hair cosmetic using 50% neutralization ratio polymer complex: A precipitate was observed after three months from preparation of this hair cosmetic. Bad storage stability.

Hair cosmetic using 170% neutralization ratio polymer complex: Bad hair set retaining and sticky to the touch.

Example 4

A hair cosmetic having the following composition was prepared by replacing polymer complex (1) of Example 1 with polymer complex (4) synthesized by Synthesis Example 4.

| | |
|---|---|
| Polymer complex (4) | 10 parts by weight |
| Ethanol | 30 parts by weight |
| Water | Balance of 100 parts by weight |
| Perfume | 0.1 parts by weight |
| Preservative | 0.01 parts by weight |
| EVALUATION: Good results were observed comparable to that of Example 1. | |

These examples illustrate that the combination of an amino group containing polysiloxane with an anionic polymer provided a hair cosmetic material which is comparable or superior in gloss, wetness, ease of combing and in addition, imparts in hair set retention without the reaction product forming an undesirable precipitate.

What is claimed is:

1. A hair set retaining cosmetic material comprising a reaction product prepared by:
    (1) reacting for at least three hours in a solvent at the reflux temperature of the solvent
        (A) 100 parts by weight of an amino group containing polysiloxane expressed by the following general formula:

$A_mR_{3-m}SiO(R_2SiO)_x(QRSiO)_ySiR_{3-n}A_n$ wherein
        A is selected from the group consisting of a hydroxyl group, an alkoxy group, and an amino containing alkyl group;
        R is selected from the group consisting of an alkyl group having 1 to 18 carbon atoms;
        Q represents an amino group containing alkyl group;
        m and n each represent a number of 0–3;
        x represents a number 300–400; and
        y represents a number of 1–30; with
        (B) 20 to 5,000 parts by weight of an anionic group containing polymer selected from the group consisting of 1-ethenyl-2pyrrolidinone, homopolymer; 1-ethenyl-2-pyrrolidinone, copolymer with acetic acid, ethenyl ester; ethene, methoxy-, copolymer with but-2-ene-1,4 dioc acid mono ethyl or mono butyl ester; acetic acid, ethenyl ester, homopolymer carboxylated; 2-butenoic acid, copolymer with acetic acid, ethenyl ester; 2-butenoic acid, copolymer with acetic, alkyl 2-methyl-2-propenoate; diacetone acrylamide, copolymer with alkyl 2-propenoate or with alkyl 2-methyl-2propenoate or with 2-propenoic acid or with 2-methyl-2-propenoic acid; and 1-(hydroxymethyl)-5,5-dimethyl hydantoin, homopolymer;
    (2) concentrating the reaction product of step (1) to obtain a solid mixture; and
    (3) neutralizing the reaction product of step (2) with an alkaline compound to a neutralization ratio of 60–150%.

2. A process for making a hair set retaining cosmetic material comprising:
    (1) reacting for at least three hours in a solvent at the reflux temperature of the solvent
        (A) 100 parts by weight of an amino group containing polysiloxane expressed by the following general formula:

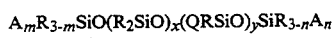

wherein
A is selected from the group consisting of a hydroxyl group, an alkoxy group, and an amino containing alkyl group;
R is selected from the group consisting of an alkyl group having 1 to 18 carbon atoms;
Q represents an amino group containing alkyl group;
m and n each represent a number of 0–3;
x represents a number 300–400; and
y represents a number of 1–30; with
(B) 20 to 5,000 parts by weight of an anionic group containing polymer selected from the group consisting of 1-ethenyl-2-pyrrolidinone, homopolymer; 1-ethenyl-2-pyrrolidinone, copolymer with acetic acid, ethenyl ester; ethene, methoxy-, copolymer with but-2-ene-1,4 dioc acid mono ethyl or mono butyl ester; acetic acid, ethenyl ester, homopolymer carboxylated; 2-butenoic acid, copolymer with acetic acid, ethenyl ester; 2-butenoic acid, copolymer with alkyl 2-methyl-2-propenoate; diacetone acrylamide, copolymer with alkyl 2-propenoate or with alkyl 2-methyl-2-propenoate or with 2-propenoic acid or with 2-methyl-2-propenoic acid; and 1-(hydroxymethyl)-5,5-dimethyl hydantoin, homopolymer;
(2) concentrating the reaction product of step (1) to obtain a solid mixture; and
(3) neutralizing the reaction product of step (2) with an alkaline compound to a neutralization ratio of 60–150%.

3. A composition according to claim 1 wherein the reaction product os step (2) is neutralized with an alkaline compound selected from the group consisting of: 2-amino-2-methyl propanol, 2-amino-2-methyl-1,3-propanediol and triisopropanol amine.

4. A composition according to claim 1 additionally comprising a cosmetic additive selected from the group consisting of: camellia oil, rapseed oil, sesame oil, safflower oil, cottonseed oil, castor oil soybean oil, coconut oil, palm off, beeswax, montanic wax, lanolin, squalane, silicone oil.

5. A composition according to claim 1 additionally comprising a surface active agent.

6. A composition according to claim 1 wherein the solvent is ethanol and the reflux temperature is eighty degrees centigrade.

7. A composition according to claim 1 wherein the reaction product of step (1) is neutralized before it is concentrated.

8. A process according to claim 2 wherein the reaction product of step (2) is neutralized with an alkaline compound selected from the group consisting of: 2-amino-2-methyl propanol, 2-amino-2-methyl-1,3-propanediol and triisopropanol amine.

9. A process according to claim 2 additionally comprising the step of adding a cosmetic additive selected from the group consisting of: camellia oil, rapseed oil, sesame oil, safflower oil, cottonseed oil, castor oil soybean oil, coconut oil, palm oil, beeswax, montanic wax, lanolin, squalane, silicone oil.

10. A process according to claim 2 additionally comprising the step of adding a surface active agent.

11. A process according to claim 4 wherein the solvent is ethanol and the reflux temperature is eighty degrees centigrade.

12. A process according to claim 2 wherein the reaction product of step (1) is neutralized before it is concentrated.

* * * * *